(12) United States Patent
Muuranto et al.

(10) Patent No.: US 6,926,675 B2
(45) Date of Patent: Aug. 9, 2005

(54) CATHETER HEATING CIRCUIT FOR CONTINUOUS CARDIAC OUTPUT MEASUREMENT

(75) Inventors: Erno Muuranto, Helsinki (FI); Juha Virtanen, Helsinki (FI)

(73) Assignee: GE Healthcare Finland Oy, Helsinki (FI)

( * ) Notice: Subject to any disclaimer, the term of this patent is extended or adjusted under 35 U.S.C. 154(b) by 407 days.

(21) Appl. No.: 10/060,013

(22) Filed: Jan. 29, 2002

(65) Prior Publication Data
US 2002/0116038 A1 Aug. 22, 2002

(30) Foreign Application Priority Data
Jan. 29, 2001 (FI) .............................................. 20010171

(51) Int. Cl.[7] .............................................. A61B 5/028
(52) U.S. Cl. ...................................................... 600/526
(58) Field of Search ................................ 600/504, 505, 600/526, 549; 607/21, 24

(56) References Cited

U.S. PATENT DOCUMENTS

| 5,594,375 A | | 1/1997 | Carlson et al. |
| 5,636,638 A | * | 6/1997 | Carlson et al. .............. 600/504 |
| 5,797,964 A | | 8/1998 | Carlson et al. |

FOREIGN PATENT DOCUMENTS

WO 93/15655 8/1993

* cited by examiner

Primary Examiner—George R. Evanisko
(74) Attorney, Agent, or Firm—Andrus, Sceales, Starke & Sawall, LLP

(57) ABSTRACT

The present invention concerns a catheter heating circuit for continuous cardiac output measurement. The circuit comprises a DC power source for supplying an operating voltage for the circuit, wherein the heating power from the heating circuit is fed to the catheter via an isolating transformer. Isolation is known per se and it is not described in detail. According to the invention the heating circuit further comprises means for generating a bipolar square wave with variable duty cycle, which square wave is supplied to said isolating transformer and further to the catheter filament.

11 Claims, 3 Drawing Sheets

CATHETER HEATING CIRCUIT FOR CONTINUOUS CARDIAC OUTPUT MEASUREMENT

CROSS REFERENCE TO RELATED APPLICATION

The present application claims priority from Finnish Application No. 20010171, filed Jan. 29, 2001.

FIELD OF THE INVENTION

The present invention relates to a clinical cardiac output measurement. In particular, the present invention relates to a novel and improved heating power source for heating the catheter filament.

BACKGROUND OF THE INVENTION

Cardiac output is the measure of the amount of blood that heart pumps each minute. Current standard for clinical cardiac output measurement is bolus thermodilution method. In the method cooled (or room temperature) indicator solution is injected into the right heart and blood temperature is measured downstream in the pulmonary artery. Cardiac output can be calculated using the obtained blood temperature curve.

With bolus thermodilution method cardiac output information is obtained only at the measurement instants. However, other hemodynamic parameters, such as blood pressure, heart rate, and blood oxygenation can be monitored continuously. Continuous measurement of cardiac output would complete the real-time picture of the hemodynamic status of the patient.

Since 1960's, there have been numerous attempts to replace indicator injection by heating the blood with a resistive heater attached to the catheter, but the accuracy and reliability of the measurement has been rather poor. During recent years, continuous thermodilution methods have developed to a level, where reliable and accurate clinical use of the method is possible and at present stand-alone monitoring devices are commercially available.

However, when it comes to the question of integrating continuous cardiac output (CCO) measurement into a modular multiparameter patient monitor, there are several points to take into account. In CCO measurement accurately regulated power source for blood heating and an accurate measurement of blood temperature at the pulmonary artery are needed.

In U.S. Pat Nos. 5,594,375 and 5,636,638 is disclosed a power source for CCO measurement. The problem of the disclosed power source is, however, that it has more than one power stages and lots of components. These make it inefficient to use and difficult to install to a small cases in the measurement systems.

The real challenges in the integration are related to the heating power source. Heating of the catheter filament requires approximately 12–15 W output power. In order to reduce the risk of ventricular fibrillation in fault conditions, the heating power is to be fed to the catheter in form of 100 kHz sine wave. Because a typical measurement module of a modular patient monitor consumes less than 2 W power, the thermal properties of the module cases are designed to handle only this amount of power dissipation. Therefore, the fundamental problem at present is to develop a heating circuit, which produces the heating signal with high efficiency. In addition, the limited space in the module sets additional constraints for electronics design.

Thus, there is an increasing need for a heating circuit that drives heating energy to the catheter filament and fits to a given small space: In one example the dimensions of the CCO heater module are 107 mm×87 mm×38 mm. The size of the module sets limits to the circuit area and used components, but even more importantly it sets limits for the heat that may be dissipated into the module case.

The objective of the present invention is to provide a circuit that meets the above-mentioned requirements.

Another objective of the present invention is to provide a heater circuit that has as high efficiency as possible, which saves from a lot of problems and costs in thermal issues.

Another objective of the present invention is to provide a heater circuit, which has as small amount of components as possible and which can be used also in connection with small size modules as mentioned above.

As for the features characteristic of the invention, reference is made to them in the claims.

SUMMARY OF THE INVENTION

Consequently, the present invention concerns a heating power source, which substantially obviates one or more of the limitations and disadvantages of the related art.

The present invention concerns a catheter heating circuit for continuous cardiac output measurement. The circuit comprises a DC power source for supplying an operating voltage for the circuit, wherein the heating power from the heating circuit is fed to the catheter via an isolating transformer. Isolation is known per se and it is not described in detail. According to the invention the heating circuit further comprises means for generating a bipolar square wave with variable duty cycle, which square wave is supplied to said isolating transformer and further to the catheter filament. The heating power to the catheter is controlled by adjusting the duty cycle of the bipolar square wave.

Thus the invention provides an easy way to implement a heating power circuit, which fulfils the above mentioned requirements.

In one embodiment of the invention said means for generating a bipolar square wave comprise a bridge circuit, which is constituted of four on/off-switches and a bridge controller, which is connected to said bridge circuit for controlling the state of said bridges according the controlling scheme specified in advance. The switches can be e.g. MOSFET transistors, which are controlled by driving signals, whose phase shift can be adjusted. The bridge controller can be e.g. a microcontroller, which is programmed according to the specific needs of the heating circuit. Advantageously the bridge controller is connected to the DC power source for measuring the output voltage of said DC power source. By this measurement the controller can take into account the changes in the operating voltage and control the bridge accordingly.

In one embodiment of the invention the heating circuit comprises a filter circuit, which is connected between said bridge circuit and said isolating transformer for filtering of harmonic overtones close to the first harmonic. There is undesired harmonic frequencies close to the base frequency of 100 kHz and therefore the filter circuit, which is advantageously a LC-filter, is optimised for giving the steepest transition from pass-band to stop-band. One possible example of the filter is Chebyshev-filter, which provides steep transition "knee" while keeping the structure of the filter simple, so that minimal amount of large size passive filter components are needed.

Blood heating inside the heart is very safety critical. Filament overheating can cause damage to the heart, which can be fatal. Therefore, the heater electronics must have independent supervision capable of heater shutdown in case of any single hardware or software malfunction. Thus, in one embodiment of the invention the heating circuit comprises a measurement circuit for measuring an information of accurate power delivered to the catheter. The measurement circuit can also include a safety switch, which disconnects supply voltage to the catheter filament in case of malfunction, e.g. filament overheating.

In one embodiment of the invention the heating circuit comprises a feedback loop for supplying to said bridge controller an information of accurate power delivered to the catheter. Advantageously the feedback is taken from the floating of the isolation transformer digitally by an isolator circuit, which can be e.g. an opto-isolator. The digital information does not suffer from component tolerances, so the bridge controller can fine-tune the control signal according to the accurate power measurement. The feedback can also be used for the safety operations to switch off the power if the catheter filament is broken or overheated. If the filament temperature exceeds a predetermined limit, the heating power is reduced or shut down. The heating power is also reduced if the flow is lower than the predetermined limit.

In one embodiment of the invention the temperature of the filament is monitored by measuring the voltage and the current applied to the catheter. The resistance of the filament is calculated from the measured current and voltage. Since the resistance of the filament varies according to its temperature, the temperature can be calculated when the resistance is known.

The benefit of the present invention is that the regulated AC supply voltage is produced in a single power stage. The supply voltage may be produced using unregulated DC power source, which reduces the amount of the needed power electronics. Furthermore this makes the circuit more efficient, reduces the size of the circuit and makes it cheaper. Furthermore the independent controlling in generating the AC signal on non-floating side of the isolation transformer and in the measurement of the amplitude on the floating side of said transformer makes the patient safety better.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings.

DETAILED DESCRIPTION OF THE INVENTION

Reference will now be made in detail to the embodiments of the present invention, examples of which are illustrated in the accompanying drawings.

Figure 1:
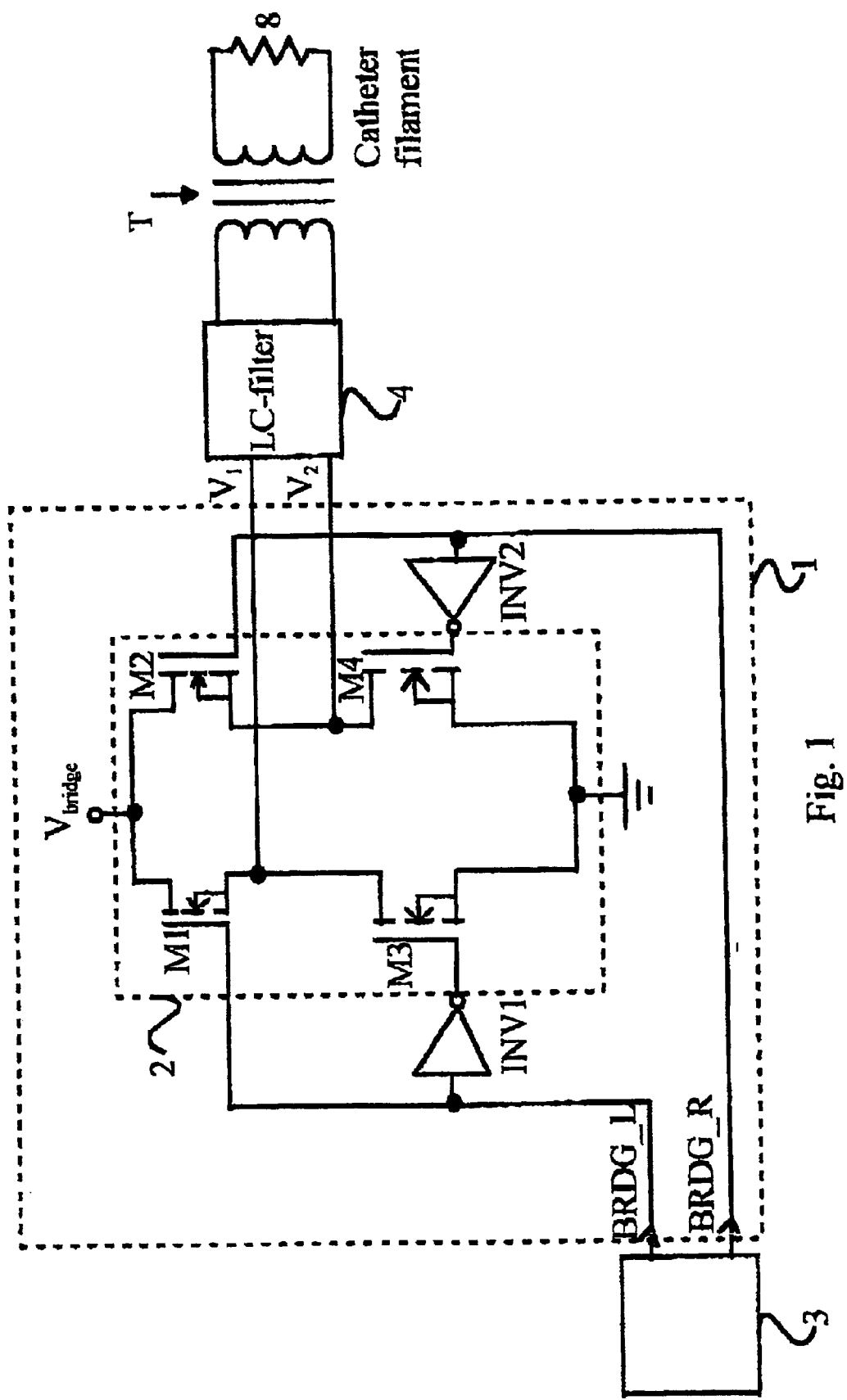
FIG. 1 is a diagram illustrating a heater circuit according to one embodiment of the present invention.
Figure 2:
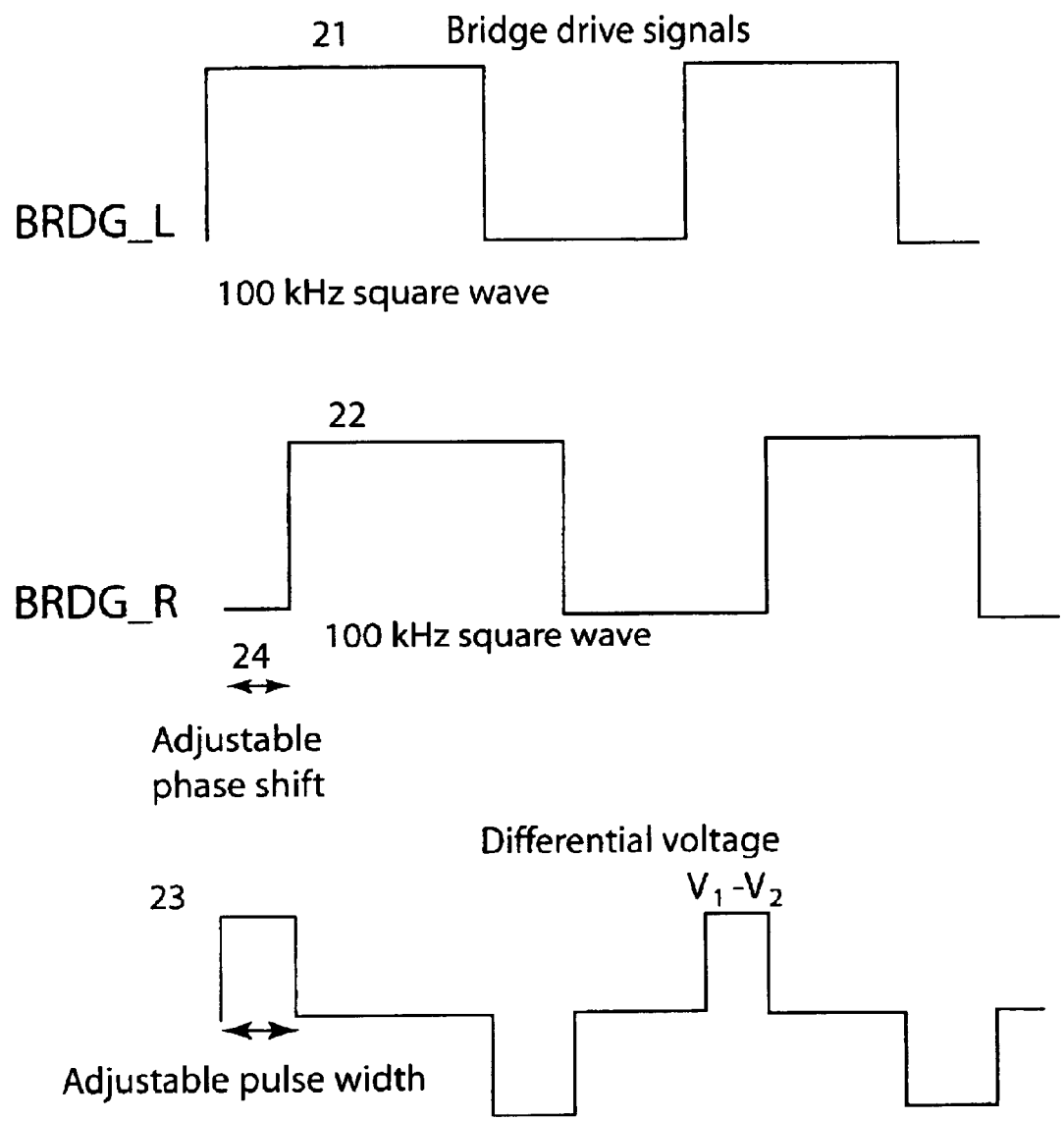
FIG. 2 is a timing diagram of the controlling signals for the heater circuit's of FIG. 1 bridge circuit according to one embodiment of the present invention.

FIG. 1 shows the bridge circuit 2 according to one embodiment of the present invention and FIG. 2 shows the driver signals from the bridge controller 3 (FIG. 3) used in waveform generation. Both sides (M1, M3 and M2, M4) of the bridge are controlled independently with signals BRDG_L and BRDG_R. Driving signals to the low side MOSFETs M3, M4 are generated by inverting the driving signals to the high MOSFETs M1, M2. Inverters INV1 and INV2 make the inverting. This way the high side M1, M2 and low side M3, M4 MOSFETs are never conducting simultaneously. Simultaneous conducting would lead to a short circuit between supply and ground.

As FIG. 2 illustrates, both sides of the bridge are driven by 100 kHz, 50% duty cycle square waves, but as it will apparent to the man skilled in the art, other frequencies and duty cycles may be used. By controlling the phase shift between driving signals of the half bridges, the duty cycle of bipolar output waveform can be adjusted. To see this more clearly, the operation of the circuit of FIG. 1 is described in detail.

At the beginning of the waveforms in FIG. 2, the left side of the bridge M1, M3 is driven to output voltage $V_{bridge}$ to the node $V_1$ and the right side of the bridge M2, M4 is driven to output zero voltage to the node $V_2$. This leads to differential voltage $+V_{bridgw}$ across the LC-filter. A moment later, the output of the right side of the bridge is driven also to $+V_{bridgw}$, and the differential voltage across the LC-filter becomes 0. Next, the left side is brought to zero, which leads to voltage $-V_{bridgw}$ across the LC-filter. The cycle is completed when the right side of the bridge is also driven to 0 volts, which brings the differential load voltage to zero again.

The bridge circuit 2 offers low source impedance at all above-mentioned levels. When there is a differential voltage across the load, the current circuit is comprised of high side MOSFET M2-LC-filter 4-transformer T-low side MOSFET M4 of the other side of the bridge. When both sides of the bridge are brought to zero volts, the current circuit is comprised of low side MOSFET M3-LC-filter 4-transformer T-low side MOSFET M4 of the other side of the bridge. When both halves are brought high, the circuit is high side MOSFET M1-LC-filter 4-transformer T-high side MOSFET M2 of the other side of the bridge.

The switching scheme provides correct differential voltage across the LC-filter 4. There is, however, a big common mode signal, which is not desired in the load (catheter filament). Therefore, a transformer is needed to remove the common mode signal from the load signal (the transformer is needed anyway for the patient isolation and impedance matching).

The heating signal is 100 kHz sine, which is fed to the catheter at adjustable power level. The heating signal is switched on and off periodically according to the measurement algorithm. 100 kHz sine signal is used because the cardiac cells will not react to the high frequency current in case the catheter is broken and the heating signal is conducted to the heart.

Amplitude of the output sine signal depends on the duty cycle of the bipolar square wave accordingly. The amplitude is changed when the DC-voltage to the bridge is changed or the duty cycle of the bipolar square wave is changed. The duty cycle adjustment provides means for controlling the power delivered to the load. The square waves with controllable phase shift used in driving the bridge are easy to produce with a microcontroller. Since the DC-voltage to the bridge is unregulated, a means for compensating the supply voltage variations are needed.

Figure 3:
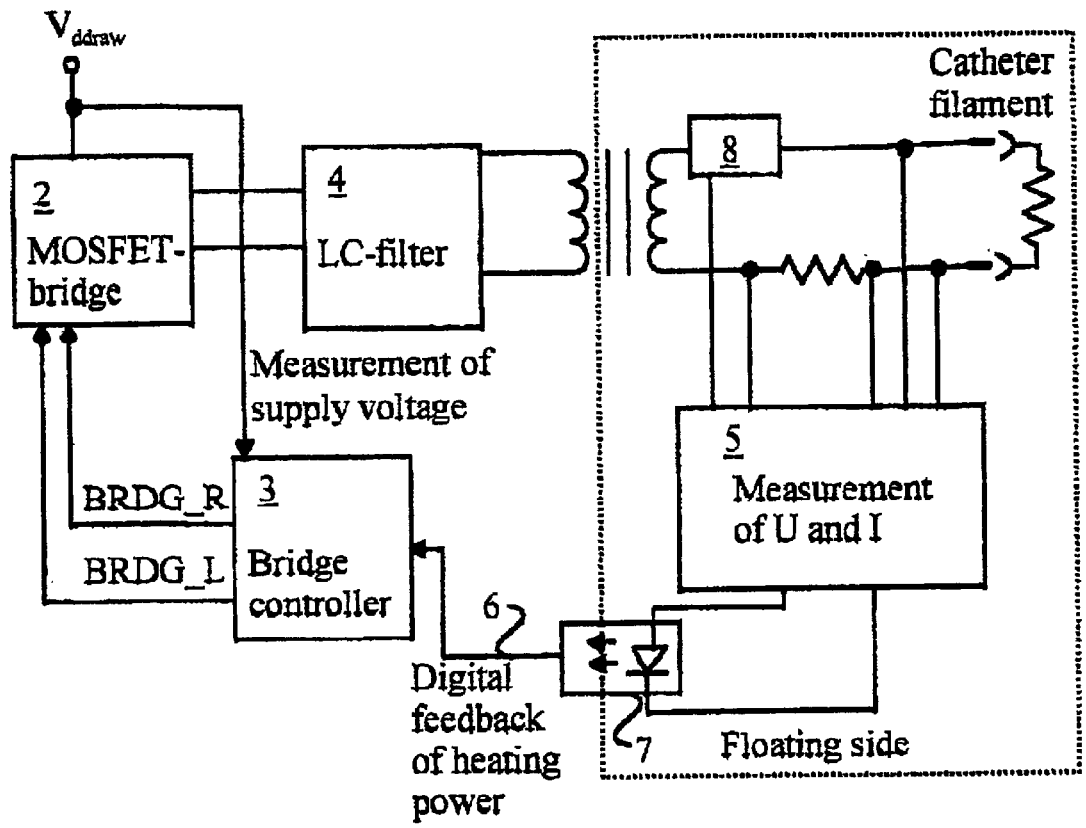
FIG. 3 is a block diagram of the heating module including a heating power circuit according to one embodiment of the present invention.

FIG. 3 shows the feedback loop 6 used in regulating the output power to the catheter. The driver signal to the bridge 2 is created in a microcontroller 3. The microcontroller 3 measures the supply voltage available to the bridge 2 and adjusts the bridge drive signal according to the supply voltage. Due to component tolerances and thermal variations in MOSFETs, LC-filter 4 and transformer, the regulation based on supply voltage measurement, which is made by a measurement circuit 5, alone will probably not reach the required 1% accuracy. Therefore, feedback is provided from the floating side electronics, which measures the accurate power delivered to the catheter. This information is sent to the bridge controller digitally through the opto-isolation 6. The digital information does not suffer from component tolerances, so the bridge driver can fine-tune the control signal according to the accurate power measurement. The measurement circuit 5 also includes a safety switch 8 for disconnecting the heating power if needed. The safety switch 8 can also be a stand-alone device, but in this embodiment it is described together with the measurement circuit 5.

It is obvious to a person skilled in the art that with the advancement of technology, the basic idea of the invention may be implemented in various ways. The invention and its embodiments are thus not limited to the examples described above, instead they may vary within the scope of the claims.

What is claimed is:

1. A catheter heating circuit for heating a catheter for continuous cardiac output measurement, the circuit comprising
    an isolation transformer couplable to the catheter;
    a single supply DC power source for supplying an operating voltage for the circuit, wherein heating power from the heating circuit is adapted to be fed to the catheter via the isolating transformer; and
    a subcircuit connected between the DC source and the isolation transformer for generating a bipolar square wave with variable duty cycle.

2. Catheter heating circuit according to claim 1, wherein the subcircuit for generating a bipolar square wave with variable duty cycle comprises
    a bridge circuit, comprising four on/off controllable switches elements, and
    a bridge controller, which is connected to said bridge circuit for controlling the state of said switching elements according to a predetermined controlling scheme.

3. Catheter heating circuit according to claim 2, wherein said catheter heating circuit further comprises
    a filter circuit, which is connected either in a non-floating side of the heating circuit between said bridge circuit and said isolating transformer or in a floating side of the heating circuit between said isolating transformer and the catheter.

4. Catheter heating circuit according to claim 2, wherein said circuit further comprises
    a measurement circuit for measuring power delivered to the catheter; and
    a feedback loop for supplying to said bridge controller an indication of the power delivered to the catheter.

5. Catheter heating circuit according to claim 2, wherein
    said bridge controller is connected to said DC power source for measuring and output voltage of said DC power source.

6. Catheter heating circuit according to claim 4, wherein said feedback loop comprises an isolator circuit for galvanically isolating said power indication delivered to the catheter.

7. Catheter heating circuit according to claim 6, wherein said isolator circuit is an opto-isolator.

8. Catheter heating circuit according to claim 2, wherein said bridge controller comprises a microcontroller and supporting circuitry.

9. Catheter heating circuit according to claim 2, wherein the that the two halves of the said bridge circuit are adapted to be controlled by identical square waves with an adjustable phase shift between them.

10. Catheter heating circuit according to claim 1, wherein said circuit further comprises
    a measurement circuit for measuring the power delivered to the catheter.

11. Catheter heating circuit according to claim 1, wherein said heating circuit further comprises a safety switch for disconnecting the heating power if needed.

* * * * *